United States Patent [19]
Teskey

[11] Patent Number: 6,099,126
[45] Date of Patent: Aug. 8, 2000

[54] SUNLIGHT SENSITIVITY TESTER

[76] Inventor: Susan Teskey, 2215 Martin Dr., Tustin, Calif. 92680

[21] Appl. No.: 09/434,145

[22] Filed: Nov. 4, 1999

[51] Int. Cl.[7] ........................................................ A61B 3/10
[52] U.S. Cl. .............................................................. 351/213
[58] Field of Search .................................... 351/205, 207, 351/213, 216, 217, 218, 221, 246

[56] References Cited

U.S. PATENT DOCUMENTS

| | | |
|---|---|---|
| 2,321,915 | 6/1943 | Higley . |
| 3,425,772 | 2/1969 | Minas . |
| 3,436,146 | 4/1969 | Minas . |
| 3,684,355 | 8/1972 | Molner . |
| 4,155,632 | 5/1979 | Wolbarsht . |
| 4,533,221 | 8/1985 | Trachtman . |
| 4,764,007 | 8/1988 | Task . |
| 4,800,404 | 1/1989 | Ginsburg et al. . |
| 5,007,730 | 4/1991 | McAllister et al. . |
| 5,381,196 | 1/1995 | Luce . |
| 5,671,039 | 9/1997 | Grolman . |
| 5,790,235 | 8/1998 | Kirschbaum .............................. 351/246 |
| 5,801,808 | 9/1998 | Abraham et al. ....................... 351/221 |

*Primary Examiner*—George Manuel
*Attorney, Agent, or Firm*—Fulwider Patton Lee & Utecht, LLP

[57] ABSTRACT

An interactive system and method for testing the sunlight sensitivity of a subject is provided herein. The system includes a computer generated imaging device for displaying a number of realistic situational scenes on a viewing screen situated opposite an observation port. The subject first views the scenes under a variety of lighting conditions created by an illumination source and indicates a level of visual discomfort through actuating a response indicator. The test is then repeated using a series of lens filters inserted between the observer and the screen and a set of new responses is recorded wherein the lens offering the most comfortable or pleasing protection against the light is determined for the subject.

15 Claims, 3 Drawing Sheets

SUNLIGHT SENSITIVITY TESTER

BACKGROUND OF THE INVENTION

1. Field of the Invention

The present invention relates to a system and method for testing an individual's sensitivity to light.

2. Description of the Prior Art

Several devices and methods have been proposed for measuring a subject's sensitivity to glare or light possessing significant intensity and prescribing tinted lenses as a result. Generally, the subject views a test pattern through an aperture or port while the intensity of a light source is increased to inhibit the visual acuity of the test subject viewing the test pattern. The subject indicates at which point the test pattern is no longer clear or visible or at which point the subject begins to experience visual discomfort and a reading is taken. Differently tinted lenses may then be inserted between the eyes of the test subject and the light source to determine if any improvement in visual acuity results. The test patterns used are generally letters, symbols, or other patterns developed in the ophthalmic industry for the special purpose of testing a subject's perception of contrasting objects.

One such effort is described in U.S. Pat. No. 3,425,772 to Minas wherein the inventor provides a device for measuring retinal irradiation or the point when the periphery of a light source appears to increase. The device itself includes a light source arrangement comprising two elongated light sources or a circle and point source configuration which are illuminated to form light peripheries. The respective light is intensified and the peripheries merge to appear as a single light source upon which event the test subject notifies the test supervisor. The irradiation point is equated to a chart generated by running a series of examinations on individuals to establish a range. A tinted lens is then prescribed to the patient to increase the intensity at which retinal irradiation occurs.

In U.S. Pat. No. 2,209,978 to Higley, the inventor produced another device of this nature called a glaremeter for determining sensitivity to glare for instance, when viewing the oncoming lights of an automobile. The glaremeter includes a housing with an aperture on one end for viewing into a compartment. Situated within the compartment is a light and reflector for focusing the rays of light onto the eyes of the observer. The observer views a series of letters appearing at the opposite end of the compartment while a second light source is gradually illuminated until the objects are visible to the observer which is announced to the test supervisor. Rotatable disks upon which are mounted differently tinted lenses are positioned within the compartment in line with one of the light sources and a light meter reading is taken. Differing colored lenses are rotated between the light source and light meter to reduce the light meter's reading and determined the proper lens prescription.

Other devices of this nature can also be found in U.S. Pat. Nos. 5,007,730 to McAllister; 4,800,404 to Ginsburg et al.; 4,764,007 to Task; and 3,684,355 to Molner. In general, the test subject views a test pattern such as letters or other symbols through an aperture or viewing port of a box while a glare source is increased to obscure the viewer's vision at which point the viewer indicates that the target is no longer clear or visible. Lenses may then be used to reduce the glare effects.

Yet another attempt at this type of device is the Sunglass Doctor™, distributed by Brain Power, Inc., which is understood to be intended to reveal which sunglass lens best protects a patient's eyes. A device is provided to produce a test pattern as the test subject focuses on this pattern while holding a release button. A light source is gradually increased and the patient releases the button when the test pattern is no longer visible. The release of the button triggers a meter to provide a percentage density as an indication of the recommended solar prescription.

A common theme carried throughout the above-mentioned efforts is that they are all missing the ability to simulate realistic situations in which sunlight is encountered. Instead, these devices merely provide a test pattern or target consisting of alphanumeric characters or symbols established within the ophthalmic industry to have well known features for providing varying degrees of contrast and requiring varying degrees of visual acuity to perceive them. A variable intensity light source is then introduced to obscure the observer's visual acuity. Thus, the introduced glare emanates from a single source instead of multiple sources that occur in outdoor settings.

However, the settings in which sunglasses are used are typically outdoors during recreational activities with a wide range of stimulus presenting itself to the sunglass wearer. In other words, blinding glare often arises from a variety of sources and not merely a single point light source such as a headlight. Additionally, the above-references devices are also primarily focused on prescribing different tinted lenses as opposed to determining the optimum color of a lens under a variety of reflective and glare conditions.

What is still needed therefore, is a testing apparatus that conveniently presents realistic images and facilitates the determination of the proper color and tint of sunglass lenses to maximally reduce discomfort of the test subject under all sorts of outdoor lighting conditions.

SUMMARY OF THE INVENTION

An interactive testing system is described herein which includes an imaging device for displaying computer generated images portraying a variety of outdoor scenarios upon a viewing screen set a predetermined distance from an observation area from which an observer may view the images. Further provided is an illumination source constructed to project varying degrees of intensity onto the screen resulting in possible discomfort to the observer's eyes. A response indicator controlled by the observer indicates at which point the light intensity causes such discomfort and determines the need for filtered lenses. A set of varying colored lenses may then be inserted into the view path of the observer to vary or filter the effect of the different types of light sources and increase the observer's tolerance of varying degrees of light intensity or glare to determine the optimum lens color for the test subject. During this phase of the testing the observer may indicate the optimum lens color by use of the response indicator A method for testing the sensitivity of a test subject to light and determining the proper lens color that reduces the sensitivity is also disclosed herein. The initial stage of testing involves placing an individual at an observation port a predetermined distance away from the screen of an imaging device and subjecting the eyes of the observer to a series of situational images projected onto the screen while varying the lighting to determine the individual's tolerance to varying degrees of light intensity as indicated by the individual responding to the onset of visual discomfort through a remote device. A second phase of testing is then initiated with individual colored lenses inserted into the view path of the observer to filter the lighting effects occurring at the point when the observer indicated visual discomfort. From a new set of responses, a lens is determined which best increases the individual's tolerance to varying degrees of light intensity.

Other features and advantages of the present invention will become more apparent from the following detailed description of the invention, when taken in conjunction with the accompanying exemplary drawings.

Numerous advantages and aspects of the invention will be apparent to those skilled in the art upon consideration of the following detailed description which generally provides illustrations of the invention in its presently preferred embodiments.

DETAILED DESCRIPTION OF THE PREFERRED EMBODIMENT

Figure 1:
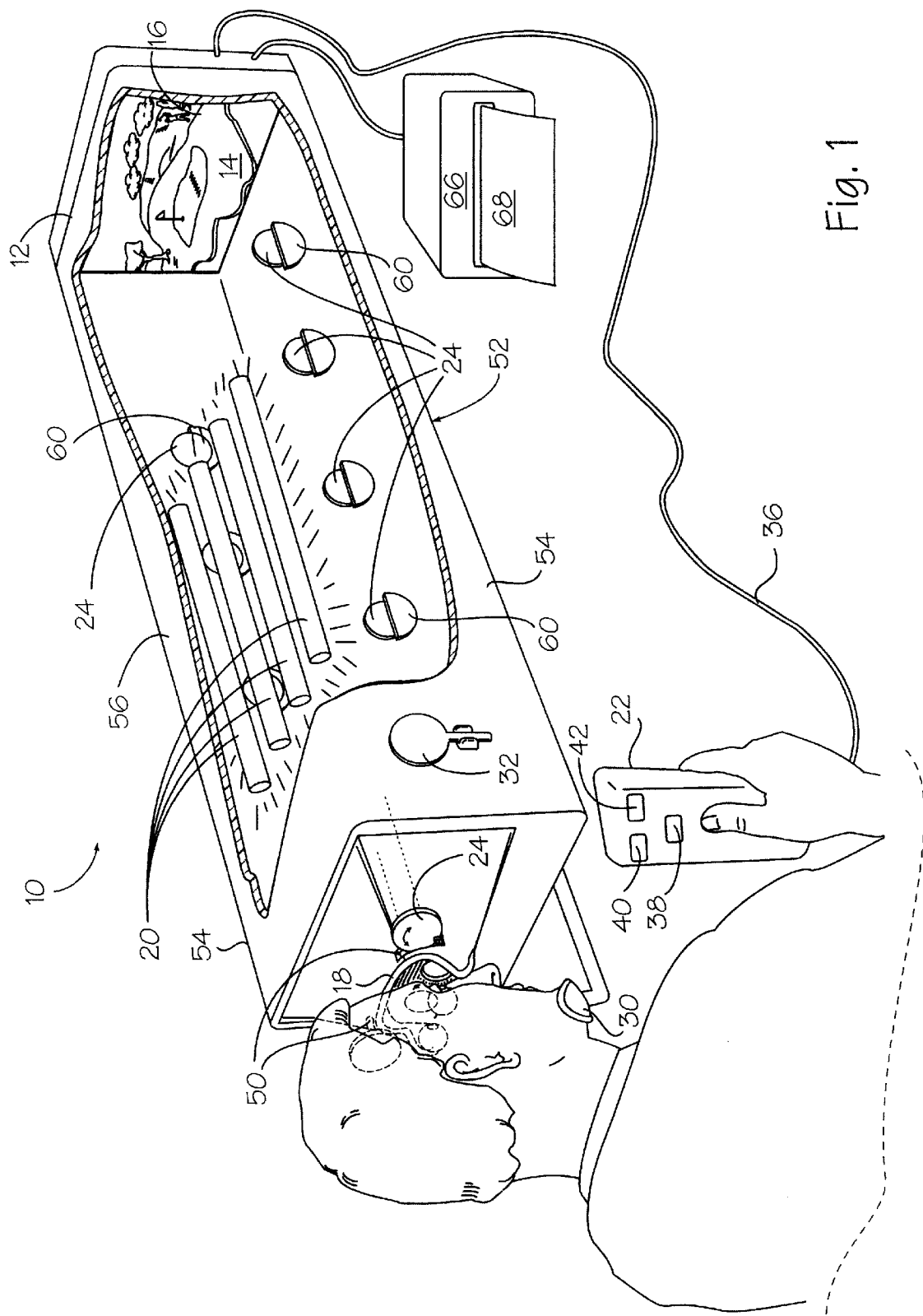
FIG. 1 is a top view of a device embodying the testing system.
Figure 2:
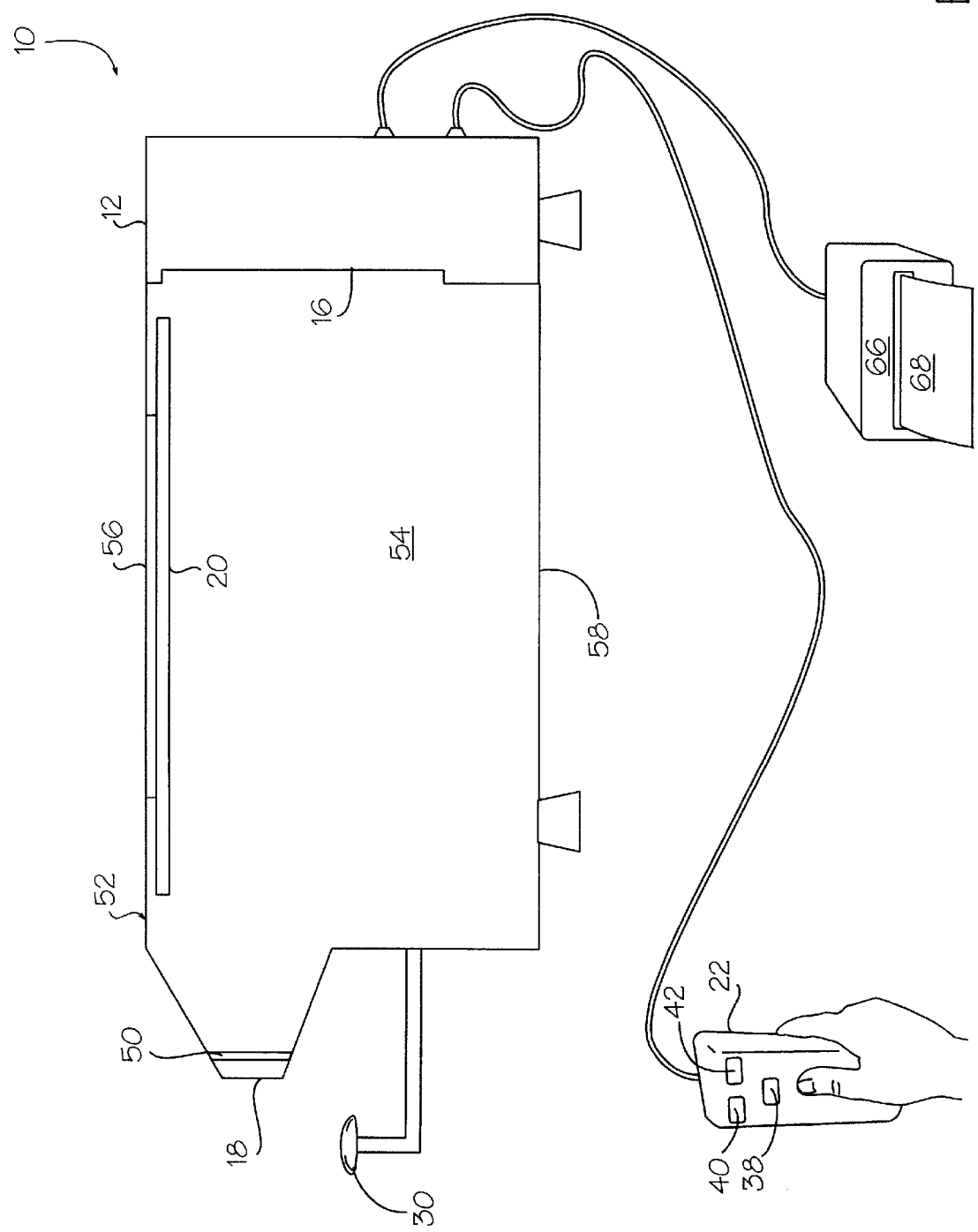
FIG. 2 is a side view of the embodiment as shown in FIG. 1 with the near side panel removed.

The present invention provides an interactive device and method for testing the degree of sensitivity a test subject has to light based upon viewing a series of preselected images under manufactured light conditions, responding upon occurrence of any discomfort, and then determining the lens color for minimizing the test subject's discomfort when subjected to such light. Referring now to FIGS. 1 and 2, the light sensitivity testing system 10 generally includes an imaging device 12 for projecting computer generated images 14 onto a screen 16, a viewing area or observation port 18 whereby the observer is positioned to view images projected onto the screen, an illumination source 20 for producing a variety of lighting effects to impact the observer's vision, a response indicator 22 for indicating discomfort to the test subject caused by the intense lighting, and a plurality of colored lenses 24, for altering the lighting effects created by the illumination source and or imaging device.

The imaging device 12 can be any conventional computer processor or other graphics imaging device commonly used in the industry to produce computer generated or virtual reality images 14 including still scenes or motion video depicting realistic scenarios involving situations wherein an observer would normally be exposed to sunlight. Common scenarios generated could involve recreational activities such as boating, bicycling, skiing, and other outdoor activities such as gardening or construction where sunlight is generally present and reflected off a variety of surfaces such as metallic objects, water, and snow. The generated images are displayed in a viewing screen or monitor 16 capable of sufficient resolution to depict such realistic scenes. The graphics capability of the imaging device must be sufficient to generate virtual reality images including a large variety of colors and include shading, reflectivity, and other lighting effects. Control of brightness and contrast of the image can be accomplished in a conventional manner through an on-screen menu or through a button driven panel on the monitor. Images that are generated will also reflect a variety of circumstances an observer will encounter throughout the day and include varying light intensities from very dim light to very bright light or glare.

The imaging device will also serve as the central processor for programming the images and receiving input from the both the test supervisor and test subject and may include an interface such as a keyboard or keypad for such activity.

Positioned opposite the viewing screen 16 at a predetermined distance away from and within the view path of the screen is an observation port 18. At this site, the observer can view the screen and observe the images 14 placed thereon. The observation port may generally take the form of a viewing window pane or be similar to a binocular eye piece as is commonly used in the ophthalmic industry. An optional chin rest 30 may be used to steady the subject's head and provide for more precise placement of the test subject. A removable eyepiece 32 or cup or other obstructive apparatus can be used to block the vision of one eye or the other to enable testing of one eye at a time if desired. The distance that the observation point is placed from the viewing screen is determined according to industry standards for eye testing and would be well known by one of ordinary skill in the industry.

In a position to cast light onto both the screen and the observer's eyes is the illumination source 20. This can be a single light or a series of lights, such as incandescent or fluorescent lights, or any light capable of producing light in the visible spectrum and powered by conventional means. The lights are constructed with variable intensity settings and may be controlled through such means as a dimmer switch commonly known throughout the electrical industry. It will be appreciated that other conventional means could be used to vary the intensity of the lighting. While the light source itself may be sufficient to cause discomfort to the viewer, alternate sources of irritation are also inherent in the system. For instance, the reflective glare off the screen from the illumination source may cause some discomfort. Additionally, the computer generated images may produce an amount of discomfort due to the brightness programmed into the images. All of these sources of light will test the subject's sensitivity to light. Alternatively, with today's technology, it may be possible to rely solely on the computer generated images for the manufactured lighting effects for testing of the subject's eyes. In other words, the brightness and reflectivity commonly found in outdoor situations could be simulated by the computer.

The response indicator 22 is typically in the form of a remote control device that may either be completely separate from the imaging device 12 and rely on radio or infrared signals to input responses to the imaging device. Alternatively, the remote control device may be connected to the imaging device via some type of cable means 36. For example, the response indicator could be in the form of a computer mouse having at least one button to allow the test subject to actuate the button and indicate that discomfort is currently being felt at a particular time in the testing. The mouse as well as other devices that are contemplated could easily include a plurality of buttons or other actuators to control the sequence of imagery viewed by the observer. For instance, the embodiment as illustrated in FIG. 1 incorporates a three button remote control device 22. An indicator button 38 is depressed or otherwise actuated when the light causes any discomfort to the observer. A forwarding button 40 allows the observer to go to the next image or series of images and a reversing button 42 enables the observer to return to previously viewed images. It will be appreciated that other forms of remote control devices could be used and be within the scope of the present invention. Instead of buttons, a dial, trackball, keypad or similar input device could be used to control the sequencing of the images and the indications of discomfort. The remote control device could also be separated into components wherein the patient has the indicator button and the test supervisor controls the imaging sequences.

A set of differently colored lenses 24 is supplied with the system. The lenses are generally circular in form to simulate sunglass lenses. Other shapes and forms may also be used provided the light is filtered through the lens prior to striking the observer's eye when the lens is in place. Colors are preferably chosen from a group of lenses colored grey, brown, green, blue, gold, silver, POLAROID® gray, POLAROIDS® brown, and POLAROID® green. It is further contemplated that some of the lenses as desired may included mirrored surfaces in addition to the coloration. Other colors and tints may also be incorporated into lenses for testing the subject if necessary. After an individual color is determined to provide the maximum comfort level, then varying tinted lenses in that color spectrum may be experimented with for further enhanced protection.

The lenses may be inserted into a slot 50 constructed to releasably retain the lens slightly in front of the subject's eyes in the observation port to filter the light projected onto the observer's eyes. Alternatively, the lens filter could be manually held between the observer and the screen. Each lens is capable of assuming two positions during testing. The initial position of each lens is out of the view path of the observer. In the second stage of testing, each individual lens may be selected and positioned within the view path of the observer to filter out irritating lighting characteristics. When testing with a particular lens is finished, that lens may be returned to the initial position out the view path of the observer.

Figure 3:
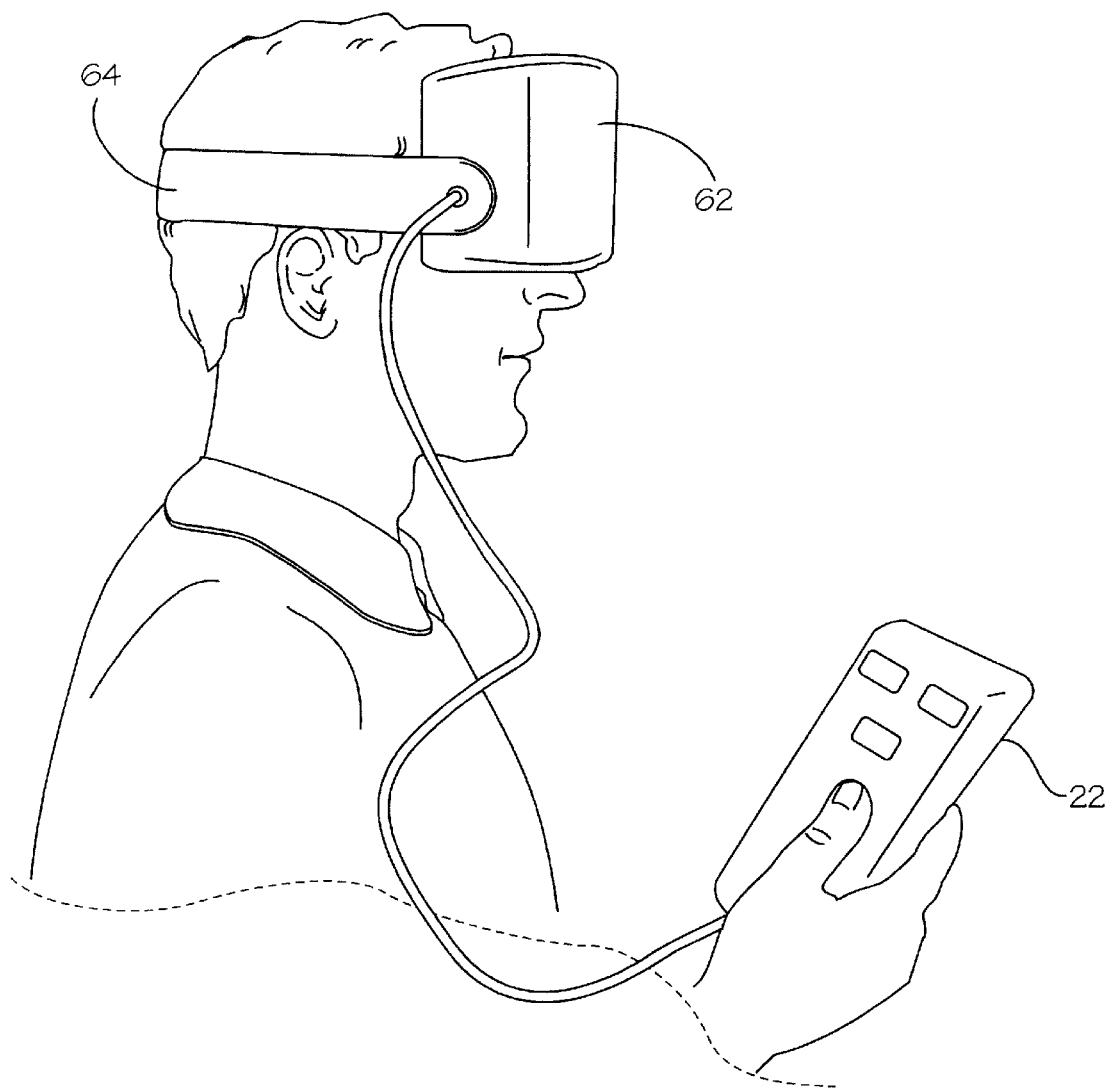
FIG. 3 depicts an alternate embodiment of the testing system in the form of headgear.

A housing, generally designated 52, may be optionally supplied to carry all the above referenced components and provide enhanced control of the lighting effects. The housing is generally an elongated structure for controlling lighting characteristics by blocking out ambient light unless desired by the test controller or supervisor. A pair of side panels 54 connects the imaging device 12 at one end to the observation port 18 at the opposing end. A top panel 56 is positioned at right angles to the two side panels and supports the illumination source at a position between the observation port and the viewing screen. A bottom panel 58 may also be provided to complete the housing and provide legs or other supports for placement on a flat surface. The respective panels can be a singular unit or held together through conventional fasteners such as threaded screws and brackets. The entire housing unit may be dimensioned for placement on a flat surface such as table or could be larger to fill up a small room and form a testing booth. A slot 50 for insertion of the lenses in a position between the observer's eyes and the viewing screen to reduce the lighting effects causing discomfort is also provided. A series of holding slots 60 can be placed in the side panels to accommodate storage of the lenses in the first position out of the view path of the observer. It will be appreciated that the shape of the housing is not critical and merely functions to carry all the components in a convenient unitary structure. For instance, the housing could be in the form of headgear 62 held in place by a head strap 64 (FIG. 3), commonly used in the virtual reality industry and all of the components discussed herein contained in the headgear.

The testing system also preferably includes some type of recording means (not shown). While manual means may be used, it is preferable to take advantage of the power of the imaging device if it is in the form of a computer processor, to be programmed to keep track of the images being viewed, light intensity offered to the observer, and the point at which the observer indicates the light causes discomfort to the individual's eyes. Programming of such factors is within the skill level of one of ordinary skill in the computer industry. Consequently, when the lenses are used in the second stage of testing, it will be a simple matter to reset the image and intensity that initially caused discomfort to the observer for consistency.

In addition to the recording means, the system 10 may also incorporate a printing means 66 for display of the recorded material to the test supervisor. Any conventional printer may be used to interface with the imaging device to produce the recorded results in printed format such as printer paper or computer tape 68.

Testing of the subject takes place in two stages. For purposes of this description, it will be assumed that the illumination source will be used in addition to the screen images. In the initial stage to determine whether the test subject needs sunglasses at all, the subject is placed at the chin rest 30 to situate the individual's eyes near the observation port 18 at a predetermined distance from the viewing screen 16. The response device 22 or discomfort indicator is placed within the control of the test subject. More specifically, the test subject places a finger on the button in a ready position and views the screen. After initially interviewing the test subject or patient to find out what type of outdoor activity or work is usually engaged in, the test supervisor or doctor presents a computer generated image 14 to the test subject based on the interview. The initial image shown to the test subject at the beginning of the test would preferably include minimal light intensity and depict an outdoor scene wherein sunlight may be encountered. A separate light source 20 is then activated and the different light characteristics such as intensity are controlled by the test supervisor. The test subject may have no discomfort when viewing this image and more images may be introduced through the use of the forward 40 and reverse 42 buttons on the remote device. The levels of intensity and reflectivity may be varied in the image or by increasing the intensity of the illumination source.

If, however, the test subject is sensitive to the brightness of the light and the light causes discomfort as indicated by not being able to stare at the image more than a brief moment in time or the test subject is not able to see a clear image, the test subject may depress the button 38 or otherwise indicate discomfort and turn away or close the eyes. The recorder means then records the image and light intensity occurring at that moment. If no discomfort is indicated, the light is intensified and the process repeated. The computer generated images cycle through a variety of outdoor activities including activities where there is a high degree of reflectivity such as occurring in water sports or snow related activities. The test subject either indicates discomfort upon viewing a particular image or does not. Based upon the light reading at the time that discomfort is indicated by the test subject, the test supervisor or a computer records the point of discomfort and compares it to a scale which may developed through the testing of multiple subjects and normalizing the results as would be understood by one skilled in the ophthalmic industry. Preferably, the scale indicates degrees of sensitivity such as no or minimal discomfort wherein sunglasses are most likely not required, to mild sensitivity, moderate sensitivity, and extreme sensitivity.

It will be appreciated that a more precise scale may be incorporated as is well known in the art. For instance, a conventional light meter could be used to develop a more detailed schedule of discomfort points. After determining the level at which discomfort occurs in a particular virtual image scene, a new scene is presented to the test subject and the process repeated to determine the discomfort level in that scene and each individual scene. The result is a report either generated by the test supervisor or a computer that may be used to keep track of discomfort levels and related scenes to produce a matrix or database of discomfort levels. Note that care is taken to instruct the test subject to indicate as soon as any discomfort is initiated and the source is rapidly removed to prevent any damage to the patient's eyes. After determining that the subject needs sunglasses in at least one situation, the second stage of testing is initiated.

Based upon the first stage results, the test supervisor resets the image and light intensity causing the initial discomfort and then inserts a lens 24 of a predetermined color near the test subject's eyes in the slot 50 to filter the lighting effects from the illumination source 20 and the image 14. The test subject then indicates if any discomfort occurs with the filter 24 in place by depressing the indicator button 38. If no discomfort occurs, then the light intensity may be varied to find a higher threshold of sensitivity with the selected lens. All scenes and light intensities where discomfort was indicated are replayed and a new set of data indicating a new set of discomfort levels with the first selected lens is produced. This is repeated for the entire set of lenses as determined by the test supervisor. Based upon the new sensitivity thresholds as developed by testing each colored lens, the test supervisor will then provide a prescription for a lens that best accommodates the subject's intended outdoor activity. If desired, once the best lens color is selected, varying tints of that color may be substituted into the process for a even more particularized prescription.

While several forms of the present invention have been illustrated and described, it will also be apparent that various modifications may be made without departing from the spirit and scope of the invention.

What is claimed is:

1. An interactive system for testing sensitivity to light comprising:
    an imaging device including a viewing screen for presenting a plurality of computer generated images to an observer;
    an observation point placed at a predetermined distance from said screen wherein the observer may view said images;
    an illumination source positioned proximate said viewing screen and constructed to project different degrees of light intensities onto said screen;
    a response device remotely connected to said imaging device and including an actuator, by which, the observer may indicate discomfort due to particular illumination; and
    a plurality of lenses constructed to assume a non-operative position whereby the observer directly views said image and a working position whereby at least one lens can be selectively positioned between said observer and said viewing screen for altering the intensity of light received by the eyes of said observer.

2. A testing system as set forth in claim 1 wherein:
    said response indicator includes an image selection button wherein said images may be selectively controlled by said observer.

3. A testing system as set forth in claim 1 further including:
    a housing having a first end for supporting said imaging device and an opposing end for mounting said observation point, said housing further supporting said illumination source and said lenses.

4. A testing system as set forth in claim 3 further including:
    a headgear strap connected to said housing and wherein said housing is dimensioned to be held on the observer's head by said headgear.

5. A testing system as set forth in claim 1 further including;
    a computer for recording actuations of said response indicator and displaying the results of multiple actuations.

6. A testing system as set forth in claim 5 further including;
    a printer for printing out said results.

7. A testing system as set forth in claim 1 wherein:
    each of said lenses is formed with a different color.

8. A testing system as set forth in claim 7 wherein:
    said colors are selected from the group consisting of grey, brown, green, blue, gold, silver, POLAROID® gray, POLAROID® brown, and POLAROID® green.

9. A testing system as set forth in claim 1 wherein:
    at least one of said lenses is mirrored.

10. A testing system as set forth in claim 1 wherein:
    said images depict scenarios having a plurality of glare conditions caused by differing reflective elements.

11. A testing system as set forth in claim 10 wherein:
    said reflective elements are selected from the group of snow, water, and mirrored objects.

12. A testing system as set forth in claim 1 wherein:
    said observation point includes a cover for covering an eye of said observer whereby the opposing eye may be tested alone.

13. An interactive light sensitivity testing system comprising:
    an imaging device including a viewing screen for presenting a plurality of virtual reality images to an observer;
    an illumination source positioned to project light onto said screen for varying the type and intensity of light delivered to the images;
    a control device for controlling the particular image to be viewed and for varying the type and intensity of light delivered to the image;
    an indicator means whereby a viewer may indicate when the illumination creates visual discomfort;
    recording means for recording the image and illumination intensity for which the viewer indicated visual discomfort to produce recorded results;
    output means for displaying the recorded results;
    a plurality of lenses, each of said lenses being of a different color, said lenses being capable of being moved from a first position, out of the view path to a second position in the view path; and
    wherein said control device, recording means, and output means are electrically connected to said imaging device.

14. An interactive testing system for determining an observer's sensitivity to varying light intensities comprising:
    a central processor for generating graphical displays based on virtual reality images having varying lighting characteristics and providing a first illumination source;
    a viewing screen constructed to display said virtual reality images;
    an observation port constructed for allowing observer to use at least one eye to view said images;

a second illumination source capable of being selectively operable to project additional light intensities on the eyes of said observer;

a remote control device remotely linked to said processor whereby the observer may selectively control the order of images and indicate undesirable lighting characteristics;

a plurality of lenses, each lens having a different color;

a housing element for supporting said processor, said viewing screen, said second illumination source, said observation port at a predetermined distance from said viewing screen, and said lenses wherein each lens can be selectively positioned in a first position out of the view path of the observer and a second position in the view path of the observer.

15. The method of measuring the light sensitivity of a test subject and determining a lens color that reduces the test subject's discomfort to the light comprising the steps of: providing a testing apparatus having a viewing area constructed to display virtual reality images, an observation port positioned at a predetermined distance from said viewing area, an illumination source proximate said viewing area, a response indicator device, and a plurality of light altering lens filters;

positioning the eyes of the test subject at said observation port;

displaying a series of said images in said viewing area for observation by the test subject;

varying the intensity of said illumination source to create different degrees of glare during observation by the test subject;

determining a discomfort level caused by said glare as indicated by actuation of said response indicator by said test subject; and repeating said displaying, varying, and determining steps with each of said colored filters inserted between the observer point and said viewing area whereby the observer selects a preferred lens color.

* * * * *